United States Patent
Nomura et al.

(10) Patent No.: US 11,426,086 B2
(45) Date of Patent: Aug. 30, 2022

(54) BLOOD PRESSURE MEASURING APPARATUS

(71) Applicant: NIHON KOHDEN CORPORATION, Tokyo (JP)

(72) Inventors: Ei Nomura, Tokyo (JP); Takashi Usuda, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 704 days.

(21) Appl. No.: 15/746,263

(22) PCT Filed: Jul. 20, 2016

(86) PCT No.: PCT/JP2016/003403
§ 371 (c)(1),
(2) Date: Jan. 19, 2018

(87) PCT Pub. No.: WO2017/013878
PCT Pub. Date: Jan. 26, 2017

(65) Prior Publication Data
US 2018/0206745 A1    Jul. 26, 2018

(30) Foreign Application Priority Data
Jul. 22, 2015  (JP) .............................. JP2015-144897

(51) Int. Cl.
*A61B 5/022* (2006.01)
*A61B 5/021* (2006.01)
*A61B 5/0235* (2006.01)

(52) U.S. Cl.
CPC ........ *A61B 5/02233* (2013.01); *A61B 5/0235* (2013.01); *A61B 5/02141* (2013.01); *A61B 2503/045* (2013.01)

(58) Field of Classification Search
CPC .................. A61B 2503/045; A61B 5/0235
(Continued)

(56) References Cited

U.S. PATENT DOCUMENTS 4,969,466 A   11/1990  Brooks
6,171,254 B1   1/2001  Skelton
(Continued)

FOREIGN PATENT DOCUMENTS

EP   0 122 123 A2   10/1984
EP   1 591 061 A1   11/2005
JP   2002-34938 A    2/2002

OTHER PUBLICATIONS

Int. Search Report dated Nov. 14, 2016 issued by the Int. Searching Authority in corresponding Application No. PCT/JP2016/003403 (PCT/ISA/210).
(Continued)

*Primary Examiner* — Alex M Valvis
*Assistant Examiner* — Aurelie H Tu
(74) *Attorney, Agent, or Firm* — Sughrue Mion, PLLC

(57) ABSTRACT

A pressurizing/depressurizing section (4) performs at least one of air feeding to a cuff (20) by way of an air way (3) and air discharging by way of the air way (3) to thereby increase or decrease an internal pressure of the cuff (20). A first controlling section (5) causes the pressurizing/depressurizing section (4) to initiate the air feeding while performing the air discharging to thereby cause the internal pressure to transit from a pressure transient state to a pressure steady state or from the pressure steady state to the pressure transient state. A determining section (6) determines Whether the internal pressure has transited to the pressure steady state by way of the pressure transient state. A second controlling section (7) causes the pressurizing/depressurizing section (4) to suppress or stop the air discharging while continuing the air feeding, in accordance with determination made by the determining section (6).

8 Claims, 2 Drawing Sheets

(58) Field of Classification Search
USPC .......................................................... 600/490
See application file for complete search history.

(56) References Cited

U.S. PATENT DOCUMENTS

| | | | |
|---|---|---|---|
| 11,058,306 B2* | 7/2021 | Nomura | A61B 5/02141 |
| 2004/0171943 A1 | 9/2004 | Hersh et al. | |
| 2009/0030329 A1* | 1/2009 | Tanabe | A61B 5/021 |
| | | | 600/500 |
| 2011/0118613 A1* | 5/2011 | Yokoyama | A61B 5/022 |
| | | | 600/486 |
| 2011/0144507 A1* | 6/2011 | Sano | A61B 5/02233 |
| | | | 600/499 |
| 2012/0059267 A1* | 3/2012 | Lamego | A61B 5/022 |
| | | | 600/483 |

OTHER PUBLICATIONS

Written Opinion dated Nov. 14, 2016 issued by the Int. Searching Authority in corresponding Application No. PCT/JP2016/003403 (PCT/ISA/237).

"Medical electrical equipment—Part 2-30: Particular requirements for the basic safety and essential performance of automated non-invasive sphygmomanometers" International Standard, IEC 80601-2-30, ISBN 2-8318-1025-0, 2009, 112 pages total.

* cited by examiner

BLOOD PRESSURE MEASURING APPARATUS

TECHNICAL FIELD

The present invention relates to a blood pressure measuring apparatus configured to measure blood pressure of a subject by use of a cuff.

BACKGROUND ART

In this kind of blood pressure measurement, cuffs having different volumes are used in accordance with categories of subjects including adults, children and neonates. Internal pressure of a cuff suitable for measurement of blood pressure differs from one category of subjects to another. Generally, the value of the internal pressure suitable for a child cuff is higher than the value of the internal pressure suitable for a neonate cuff, and the value of the internal pressure suitable for an adult cuff is higher than the value of the internal pressure suitable for the child cuff. Therefore, it is necessary to avoid a situation that the internal pressure of the neonate cuff is set at the value suitable for the adult cuff.

In consideration of the aforementioned situation, target values of the internal pressures of the cuffs are set correspondingly to the categories of the subjects or the cuff types. For example, the maximum value of the internal pressure of the neonate cuff for newborn babies is set at 150 mmHg (see Non-Patent Literature 1). In an apparatus described in Patent Literature 1, control is performed to stop or suppress pressurizing operation so as to prevent the internal pressure of the cuff from exceeding the target value, while monitoring the internal pressure of the cuff.

CITATION LIST

Patent Literature

[PTL1] U.S. Pat. No. 4,969,466

Non-Patent Literature

[NPL1] IEC 80601-2-130 (particularly see 201.12.1.104)

SUMMARY OF INVENTION

Technical Problem

Even when the pressurizing operation performed by a pressurizing mechanism such as a pump is stopped or suppressed, the internal pressure of the cuff does not immediately stop increasing due to inertia of the mechanism or air. Therefore, it is necessary to predict a timing at which the internal pressure of the cuff will reach the target value and to stop or suppress the pressurizing operation prior to the predicted timing. For example, when the increase rate of the internal pressure of the cuff is measured in real time during a pressurizing process, the timing at which the internal pressure of the cuff will reach the target value can be predicted based on the measured value.

In order to establish such prediction, temporal change (pressurizing rate) of the internal pressure of the cuff during the pressurizing process has to be linear. However, there is a case in which the change is non-linear. In such a case, it is difficult to predict the timing at which the internal pressure of the cuff will reach the target value. When the pressurizing operation is stopped or suppressed prior to a proper timing, blood pressure of a subject whose systolic blood pressure is relatively high may not be able to be measured properly. When the pressurizing operation is stopped or suppressed later than the proper timing, there may occur a problem of excessive pressurization.

An object of one aspect of the invention is to provide a blood pressure measuring apparatus wherein accuracy of pressurization control of internal pressure of a cuff is improved.

Solution to Problem

According to one aspect of the invention, there is provided a blood pressure measuring apparatus configured to measure blood pressure of a subject by use of a cuff, comprising:

a connecting section to which a tube communicating with the cuff is connected;

an air way communicating with the connecting section;

a pressurizing/depressurizing section configured to perform at least one of air feeding to the cuff by way of the air way and air discharging by way of the air way to thereby increase or decrease an internal pressure of the cuff;

a first controlling section configured to cause the pressurizing/depressurizing section to initiate the air feeding while performing the air discharging to thereby cause the internal pressure to transit from a pressure transient state to a pressure steady state or from the pressure steady state to the pressure transient state;

a determining section configured to determine whether the internal pressure has transited to the pressure steady state by way of the pressure transient state; and a second controlling section configured to cause the pressurizing/depressurizing section to suppress or stop the air discharging while continuing the air feeding, in accordance with determination made by the determining section.

With the above configuration, the first controlling section controls the operation of the pressurizing/depressurizing section so that the pressure inside the flow path including the air way and the tube can be constant prior to the pressurizing operation performed by the second controlling section. Thus, the timing at which the internal pressure of the cuff will reach the target value can be easily predicted so that the pressurizing operation can be stopped or suppressed at a proper timing. Accordingly, it is possible to provide a blood pressure measuring apparatus wherein accuracy of pressurization control of the internal pressure of the cuff is improved.

DESCRIPTION OF EMBODIMENTS

Figure 1:
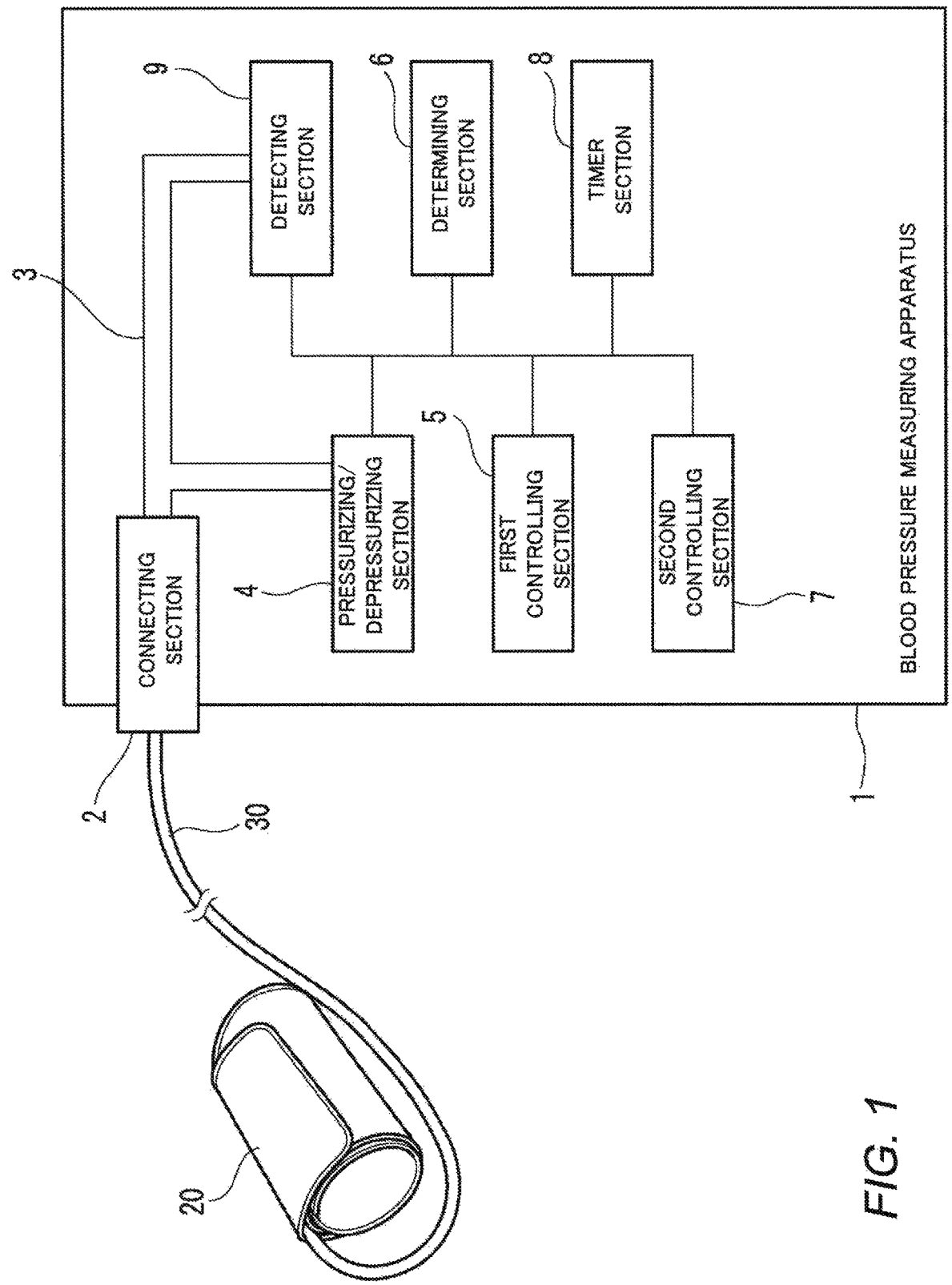
FIG. 1 is a diagram illustrating the functional configuration of a blood pressure measuring apparatus according to one embodiment.

FIG. 1 illustrates the functional configuration of a blood pressure measuring apparatus 1 according to one embodiment. The blood pressure measuring apparatus 1 is configured to measure blood pressure of a subject by use of a cuff 20. The blood pressure measuring apparatus 1 may include a connecting section 2, an air way 3, a pressurizing/depressurizing section 4, a first controlling section 5, a determining section 6, and a second controlling section 7. A tube 30 communicating with the cuff 20 is connected to the connecting section 2.

The air way 3 communicates with the connecting section 2 and the pressurizing/depressurizing section 4. The pressurizing/depressurizing section 4 is configured to execute at least one of air feeding to the cuff 20 through the air way 3 and air discharging through the air way 3 to thereby increase or reduce the internal pressure of the cuff 20.

Specifically, the pressurizing/depressurizing section 4 includes a pump function and a valve function. The pump function is to feed air to the cuff 20 through the air way 3 to thereby increase the internal pressure of the cuff 20. The valve function is to establish or block communication of ambient air with the air way 3. When ambient air is allowed to communicate with the air way 3 while the pump function is deactivated, the internal pressure of the cuff 20 is decreased. When ambient air is allowed to communicate with the air way 3 while the pump function is activated, the increasing rate of the internal pressure of the cuff 20 is decreased. The pump function and the valve function may be implemented by an independent pump device and an independent valve device respectively. Alternatively, the pressurizing/depressurizing section 4 may be implemented by one single device having the two functions.

The first controlling section 5 is configured to control the operation of the pressurizing/depressurizing section 4 so as to cause the internal pressure of the cuff 20 to transit from a pressure transient state to a pressure steady state or from the pressure steady state to the pressure transient state. The pressure transient state means a state where the value of the internal pressure of the cuff 20 is changing with time. The pressure steady state means a state where no substantial change with time can be observed in the value of the internal pressure of the cuff 20. As described above, the increase/reduction of the internal pressure of the cuff 20 can be achieved by a suitable combination of the pump function and the valve function. The first controlling section 5 is configured to adjust contribution ratios of the pump function and the valve function in the pressurizing/depressurizing section 4 to thereby cause the internal pressure of the cuff 20 to transit to the pressure transient state or the pressure steady state.

In some cases, due to a non-linear temporal change in the internal pressure of the cuff, it is difficult to predict the timing at which the internal pressure of the cuff will reach the target value, as described previously. As a result of repeated examination, the inventors have found out that pressure inside a flow path including the air way 3 and the tube 30 is less apt to be constant immediately after start of pressurizing operation, and this leads to the non-linear temporal change in the internal pressure of the cuff. In other words, the inventors have found out that when the pressurizing operation is executed in a state where the pressure inside the flow path has been made constant, the temporal change in the internal pressure of the cuff can be made linear.

In this embodiment, the first controlling section 5 is configured to control the pressurizing/depressurizing section 4 to start to feed air while discharging air. By such pressurizing operation, the pressure inside the flow path including the air way 3 and the tube 30 can be made constant while the internal pressure of the cuff 20 is kept at a relatively low value. On this occasion, the internal pressure of the cuff 20 is caused to transit to the pressure steady state by way of the pressure transient state.

Figure 2:
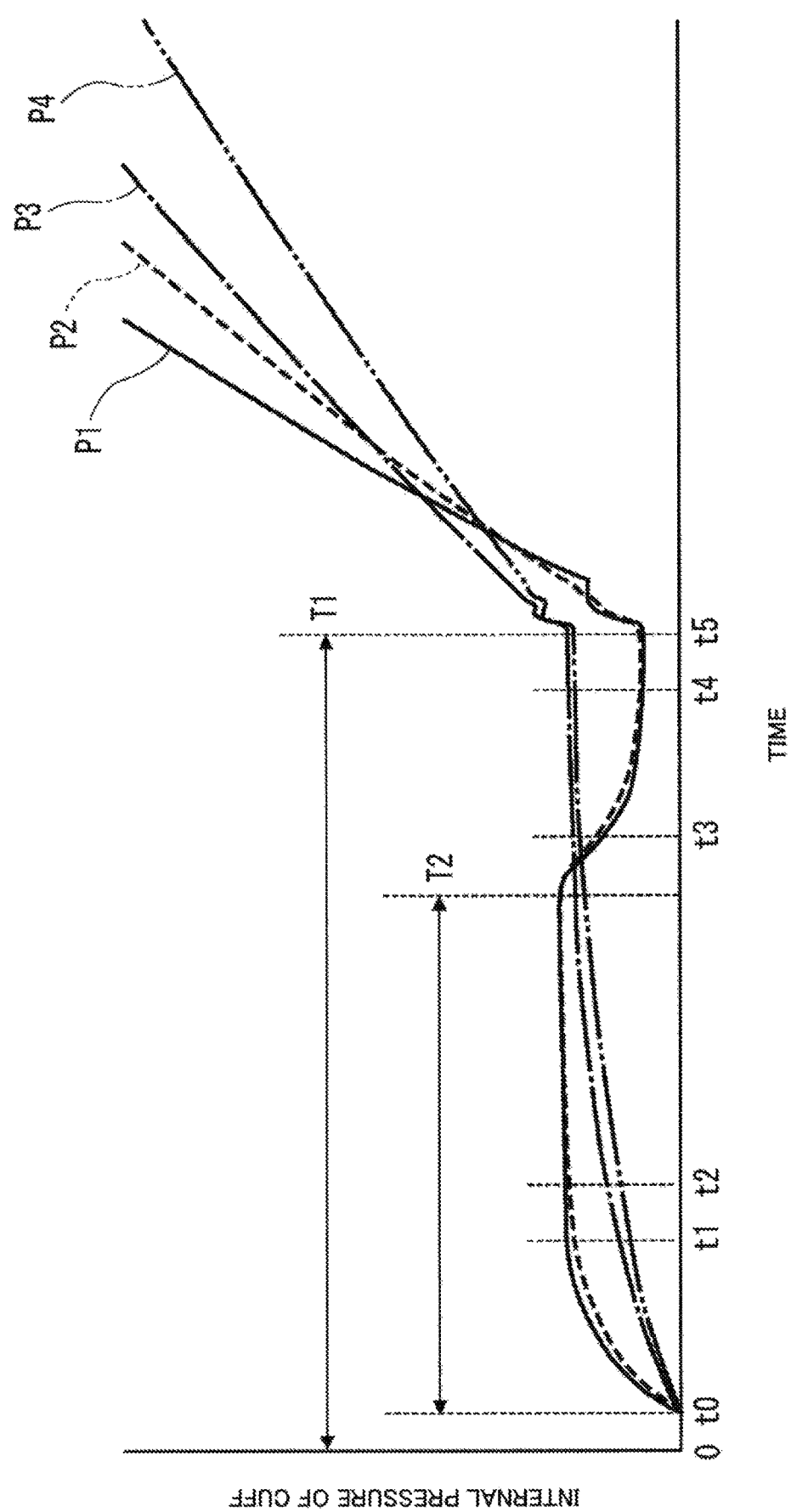
FIG. 2 is a flowchart illustrating control performed by the blood pressure measuring apparatus.

FIG. 2 illustrates temporal change of the internal pressure of the cuff 20 achieved by the blood pressure measuring apparatus 1. A solid line designates an internal pressure change characteristic P1 in a case where the cuff 20 is used as a cuff for relatively small neonates. A dashed line designates an internal pressure change characteristic P2 in a case where the cuff 20 is used as a cuff for relatively large neonates. A chain line designates an internal pressure change characteristic P3 in a case where the cuff 20 is used as a cuff for relatively small adults, A dashed chain line designates an internal pressure change characteristic P4 in a case where the cuff 20 is used as a cuff for relatively large adults.

When the pressurization by the pressurizing/depressurizing section 4 begins at a time point 0, the internal pressure of the cuff 20 begins to increase with a short delay. That is, the internal pressure of the cuff 20 is caused to transit to the pressure transient state. The internal pressure of the cuff 20 is regarded as having transited from the pressure transient state to the pressure steady state at a time point t1 in the case of the internal pressure change characteristic P1. Same or similarly, the internal pressure of the cuff 20 is regarded as having transited from the pressure transient state to the pressure steady state at a time point t2 in the case of the internal pressure change characteristic P2, at a time point t3 in the case of the internal pressure change characteristic P3, and at a time point t4 in the case of the internal pressure change characteristic P4.

The determining section 6 is configured to determine whether the internal pressure of the cuff 20 has transited to the pressure steady state by way of the pressure transient state.

The second controlling section 7 is configured to control the pressurizing/depressurizing section 4 to suppress or stop the air discharging while continuing the air feeding, based on the determination made by the determining section 6 that the internal pressure of the cuff 20 has transited to the pressure steady state by way of the pressure transient state. Specifically, an air discharging function achieved by the valve function of the pressurizing/depressurizing section 4 is made relatively lower than an air feeding function achieved by the pump function of the pressurizing/depressurizing section 4. Thus, the internal pressure of the cuff 20 begins to increase for measurement of blood pressure. Since air feeding by the pressurizing/depressurizing section 4 is maintained, seamless shift to the pressurizing process for measurement of blood pressure can be performed. Accordingly, blood pressure can be measured more rapidly.

As obvious from each of the internal pressure change characteristics P1 to P4 shown on the right side of FIG. 2, the change in the internal pressure of the cuff 20 is linear. It is because the first controlling section 5 controls the operation of the pressurizing/depressurizing section 4 so that the pressure inside the flow path including the air way 3 and the tube 30 can be constant prior to the pressurizing operation performed by the second controlling section 7. Thus, the timing at which the internal pressure of the cuff 20 will reach the target value can be easily predicted so that the pressurizing operation can be stopped or suppressed at a proper timing. Accordingly, it is possible to provide a blood pressure measuring apparatus wherein accuracy of pressurization control of the internal pressure of the cuff is improved.

More specific description will be made about how the determining section 6 determines whether the internal pressure of the cuff 20 has transited to the pressure steady state by way of the pressure transient state.

As shown in FIG. 1, the blood pressure measuring apparatus 1 may further include a tinier section 8. The timer section 8 is configured to count an elapsed time period from the start of the air feeding performed by the pressurizing/ depressurizing section 4. The determining section 6 is configured to make the aforementioned determination based on the elapsed time period counted by the timer section 8. Specifically, the determining section 6 determines that the internal pressure of the cuff 20 has transited to the pressure steady state by way of the pressure transient state when the elapsed time period counted by the timer section 8 has exceeded a predetermined time period T1 shown in FIG. 2.

The predetermined value T1 is set to be longer than a time period (time constant) until internal pressure of a cuff (P3, P4) having a largest volume among the cuffs 20 configured to be connected to the blood pressure measuring apparatus 1 transits to the pressure steady state. Specifically, the relation between the voluble V of the cuff 20 and the time (time constant) [tau] until the internal pressure of the cuff 20 transits to the pressure steady state is expressed by the following expression.

$$P = P0[1 \cdot \exp(\cdot t/[\text{tau}])]$$

$$[\text{tau}] = V \cdot R$$

Here, P is the internal pressure of the cuff 20, P0 is the internal pressure of the cuff 20 in the pressure steady state, and R is resistance of the flow path including the air way 3 and the tube 30. In a specific example, the predetermined value T1 may be 500 msec to 1,000 msec.

According to such a configuration, determination is made by the determining section 6 based on only the elapsed time period counted by the timer section 8. Accordingly, an increase in the load of a control processing of the blood pressure measuring apparatus 1 can be suppressed while the timing at which the internal pressure of the cuff 20 will reach the target value is predicted easily.

As shown in FIG. 1, the blood pressure measuring apparatus 1 may further include a detecting section 9. The detecting section 9 is connected to the air way 3. The detecting section 9 is configured to detect the internal pressure of the cuff 20. The detecting section 9 may be implemented by a pressure sensor or the like.

In addition to or in place of the determination based on the predetermined value T1 as the elapsed time period counted by the aforementioned timer section 8, the determining section 6 may be configured to determine whether the internal pressure of the cuff 20 has transited to the pressure steady state by way of the pressure transient state, based on the internal pressure of the cuff 20 detected by the detecting section 9. That is, when the internal pressure of the cuff 20 is monitored directly, the pressure transient state (state where the value of the internal pressure is changing with time) and the pressure steady state (state where no substantial change with time can been observed in the value of the internal pressure) are distinguished from each other.

According to such a configuration, determination can be made directly based on the internal pressure of the cuff 20. Accordingly, it is possible to improve prediction accuracy of the timing at which the internal pressure of the cuff 20 will reach the target value.

In this case, the determining section 6 may be configured to determine whether the internal pressure of the cuff 20 detected by the detecting section 9 shifts to a pressure steady state within a predetermined time period from start of a first pressure transient state. Based on the determination, the second controlling section 7 may be configured to control the operation of the pressurizing/depressurizing section 4 to reduce the internal pressure of the cuff 20.

Specifically, when the internal pressure of the cuff 20 detected by the detecting section 9 begins to increase immediately after the start of air feeding by the pressurizing/depressurizing section 4, the determining section 6 determines that the internal pressure of the cuff 20 has transited to a first pressure transient state. When the shift to the first pressure transient state is determined, the timer section 8 starts to count time. The time point t0 in FIG. 2 indicates a time point when the time counting is initiated.

Next, the determining section 6 determines whether the internal pressure of the cuff 20 has transited from the aforementioned first pressure transient state to the pressure steady state within the predetermined time period T2 from the time point t0. In the example shown in FIG. 2, the internal pressure of the cuff 20 has transited to the pressure steady state within the predetermined time period T2 for the internal pressure change characteristics P1 and P2 but the internal pressure of the cuff 20 has not transited to the pressure steady state within the predetermined time period T2 for the internal pressure change characteristics P3 and P4.

Various methods may be used for the determination. For example, the time period from the time point t0 to the time point t1 or t2 is counted by the timer section 8. The counted time period is compared with the predetermined time period T2 in order to make the determination. Alternatively, time period may be counted for the predetermined time period T2 from the time point to by the timer section 8 so that the determination can be made based on the value of the internal pressure of the cuff 20 detected by the detecting section 9 at the end of the time counting.

Accordingly, in the case of the internal pressure change characteristics P1 and P2, the second controlling section 7 reduces the internal pressure of the cuff 20 to be lower than a value at a time point corresponding to the lapse of the predetermined time period T2. Thus, the internal pressure of the cuff 20 is caused to transit to a second pressure transient state. Then, the internal pressure of the cuff 20 transits to a second pressure steady state. At a time point t5, the internal pressure of the cuff 20 has transited to the pressure steady state for the internal pressure change characteristics P1 and P2.

Thus, the determining section 6 determines that the internal pressure of the cuff 20 has transited to the (second) pressure steady state by way of the (second) pressure transient state. Based on the determination, the second controlling section 7 controls the pressurizing/depressurizing section 4 to suppress or stop the air discharging while continuing the air feeding. Accordingly, the internal pressure of the cuff 20 begins to increase linearly for measurement of blood pressure.

As described previously, each of the internal pressure change characteristics P1 and P2 corresponds to a neonate cuff. That is, the predetermined time period T2 may be determined in advance as a time period long enough for the internal pressure of the neonate cuff to transit to the pressure steady state under the control of the pressurizing/depressurizing section 4 made by the first controlling section 5. According to the aforementioned configuration, it is possible to suppress accumulation of oppression pressure applied by the cuff 20 on a neonate whose physical tissue strength is insufficient. In addition, the internal pressure which has been once reduced starts to be increased for measurement of blood pressure. Accordingly, measurement based on pressurization can be carried out effectively on a neonate whose blood pressure distribution is relatively low.

In the blood pressure measuring apparatus 1 according to this embodiment, the internal pressure of the cuff 20 in the pressure steady state achieved through pressurization control by the first controlling section 5 may be set to be less than 30 mmHg. Preferably, the internal pressure may be set to be less than 15 mmHg. More preferably, the internal pressure may be set to be less than 5 mmHg.

Assuming that the value of the internal pressure about determination of the cuff type is less than 30 mmHg, as in the internal pressure change characteristics P3 and P4 corresponding to the adult cuffs, measurement based on pressurization can be carried out effectively on a subject whose blood pressure distribution is relatively low, even when the internal pressure of the cuff 20 is not reduced once.

Assuming that the value of the internal pressure about determination of the cuff type is less than 15 mmHg, the internal pressure is not regarded as a "pressurizing state" on an adult as the subject in the IEC 80601-2-30:2009 standard. Thus, the apparatus is free from various constraints as to the duration etc. of the "pressurizing state" so that the degree of freedom in designing the apparatus can be improved.

Assume that the value of the internal pressure about determination of the cuff type is less than 5 mmHg. In this case, the internal pressure is not regarded as a "pressurizing state" on a neonate as the subject in the IEC 80601-2-30:2009 standard. Thus, the apparatus is free from various constraints as to the duration etc. of the "pressurizing state" so that the degree of freedom in designing the apparatus can be improved more greatly.

The aforementioned embodiments are merely exemplified in order to make the invention easy to understand. The configuration according to each of the aforementioned embodiments can be appropriately changed or modified without departing from the concept of the invention. In addition, it is obvious that equivalents are contained in the scope of the invention.

In the aforementioned embodiments, the functions of the first controlling section 5, the determining section 6, the second controlling section 7, and the timer section 8 are at least partially achieved by software executed by the cooperation of a processor and a memory which are connected to each other communicably. A CPU or an MPU may be used as an example of the processor. An RAM or an ROM may be used as an example of the memory. However, at least one of the functions of the first controlling section 5, the determining section 6, the second controlling section 7, and the timer section 8 may be implemented by hardware such as a circuit element or by a combination of hardware and software, in addition, at least two of the first controlling section 5, the determining section 6, the second controlling section 7, and the timer section 8 may be implemented by a common processor and a common memory.

The invention claimed is:

1. A blood pressure measuring apparatus configured to measure blood pressure of a subject by use of a cuff, the blood pressure measuring apparatus comprising:
a connector to which a tube communicating with the cuff is connected;
an air way communicating with the connector;
a pressurizing/depressurizing section comprising:
a pump configured to perform air feeding to the cuff via the air way to increase an internal pressure of the cuff, and
a valve configured to communicate with an ambient air to perform air discharging via the air way to decrease the internal pressure of the cuff; and
a processor configured to:
in a pressure transient state, control the pump to perform the air feeding and control the valve to perform the air discharging to cause the internal pressure to increase until the internal pressure transitions from the pressure transient state to a pressure steady state in which a pressure inside a flow path including the air way and the tube is constant;
determine that the internal pressure has transitioned to the pressure steady state from the pressure transient state; and
in response to the determining that the internal pressure has transitioned to the pressure steady state, [control the valve to suppress or stop the air discharging and control the pump to continue the air feeding to] increase the internal pressure of the cuff for measuring the blood pressure by controlling the valve to suppress or stop the air discharging and by controlling the pump to continue the air feeding.

2. The blood pressure measuring apparatus according to claim 1, further comprising:
a timer configured to measure a time period since a start of the air feeding,
wherein the processor is further configured to determine whether the internal pressure has transitioned to the pressure steady state in accordance with the time period measured by the timer.

3. The blood pressure measuring apparatus according to claim 1, further comprising:
a detector configured to detect the internal pressure,
wherein the processor is further configured to determine whether the internal pressure has transitioned to the pressure steady state in accordance with the internal pressure detected by the detector.

4. The blood pressure measuring apparatus according to claim 3, wherein the processor is further configured to:
determine whether the internal pressure detected by the detector has transitioned to the pressure steady state within a predetermined time period since a start of the pressure transient state, and
control operation of the pressurizing/depressurizing section in accordance with the determination of whether the internal pressure detected by the detector has transitioned to the pressure steady state within the predetermined time period since the start of the pressure transient state to decrease the internal pressure.

5. The blood pressure measuring apparatus according to claim 1, wherein the internal pressure of the cuff in the pressure steady state is maintained to be less than 30 mmHg.

6. The blood pressure measuring apparatus according to claim 1, wherein the pressure transient state is a state in which the internal pressure of the cuff changes with time.

7. A blood pressure measuring apparatus configured to measure blood pressure of a subject by use of a cuff, the blood pressure measuring apparatus comprising:
a connector to which a tube communicating with the cuff is connected;
an air way communicating with the connector;
a pressurizing/depressurizing section comprising:
a pump configured to perform air feeding to the cuff via the air way to increase an internal pressure of the cuff, and
a valve configured to communicate with an ambient air to perform air discharging via the air way to decrease the internal pressure of the cuff; and
a processor configured to:
in a first pressure transient state among a plurality of pressure transient states, control the pump to perform the air feeding and control the valve to perform the air discharging to cause the internal pressure of the cuff to increase until the internal pressure of the cuff transitions from the first pressure transient state to a first pressure steady state among a plurality of pressure steady states, wherein, in the first pressure steady state, a pressure inside a flow path including the air way and the tube is constant;

determine that the internal pressure of the cuff has transitioned to the first pressure steady state from the first pressure transient state and determine a first internal pressure value of the internal pressure;

in response to the determining that the internal pressure of the cuff has transitioned to the first pressure steady state, control the pump to stop the air feeding and control the valve to continue the air discharging to cause the internal pressure of the cuff to decrease, in a second pressure transient state among the plurality of pressure transient states, until the internal pressure of the cuff transitions to a second pressure steady state among the plurality of pressure steady states;

determine that the internal pressure of the cuff has transitioned to the second pressure steady state from the second pressure transient state and determine a second internal pressure value of the internal pressure of the cuff that is lower than the first internal pressure value; and in response to the determining that the internal pressure of the cuff has transitioned to the second pressure steady state, [control the valve to suppress or stop the air discharging and control the pump to perform the air feeding, to] increase the internal pressure of the cuff to be higher than the second internal pressure value for measuring the blood pressure, in a third pressure transient state to which the internal pressure of the cuff has transitioned from the second pressure steady state among the plurality of pressure transient states by controlling the valve to suppress or stop the air discharging and by controlling the pump to perform the air feeding.

8. A blood pressure measuring apparatus configured to measure blood pressure of a subject by use of a cuff, the blood pressure measuring apparatus comprising:

a connector to which a tube communicating with the cuff is connected;

an air way communicating with the connector;

a pressurizing/depressurizing section comprising:

a pump configured to perform air feeding to the cuff via the air way to increase an internal pressure of the cuff, and a valve configured to communicate with an ambient air to perform air discharging via the air way to decrease the internal pressure of the cuff; and a processor configured to:

in a period from a time of a start of the air feeding to a time before a start of a pressurizing process for a measurement of the blood pressure, control the pump to initiate the air feeding and control the valve to perform the air discharging in a pressure transient state, to cause the internal pressure to increase until the internal pressure transitions from the pressure transient state to a pressure steady state in which a pressure inside a flow path including the air way and the tube is constant;

set a predetermined time period required for the transition from the pressure transient state to the pressure steady state based on a volume of the cuff and a resistance of the flow path;

determine whether the internal pressure has transitioned to the pressure steady state from the pressure transient state within the predetermined time period; and in response to determining that the internal pressure has transitioned to the pressure steady state and based on the predetermined time period having been elapsed, [control the valve to suppress or stop the air discharging and control the pump to continue the air feeding to] increase the internal pressure for measuring the blood pressure, thereby performing the pressurizing process by controlling the valve to suppress or stop the air discharging and by controlling the pump to continue the air feeding.

* * * * *